United States Patent
Nedez

(10) Patent No.: US 7,252,768 B2
(45) Date of Patent: Aug. 7, 2007

(54) METHOD FOR ELIMINATING METAL HALIDES THAT ARE PRESENT IN A LIQUID OR GASEOUS, ORGANIC OR NON-ORGANIC EFFLUENT

(75) Inventor: Christophe Nedez, Salindres (FR)

(73) Assignee: AXENS, Rueil-Malmaison (FR)

( * ) Notice: Subject to any disclaimer, the term of this patent is extended or adjusted under 35 U.S.C. 154(b) by 0 days.

(21) Appl. No.: 10/473,987

(22) PCT Filed: Mar. 27, 2002

(86) PCT No.: PCT/FR02/01070

§ 371 (c)(1),
(2), (4) Date: Mar. 29, 2004

(87) PCT Pub. No.: WO02/081063

PCT Pub. Date: Oct. 17, 2002

(65) Prior Publication Data
US 2005/0029197 A1 Feb. 10, 2005

(30) Foreign Application Priority Data
Apr. 4, 2001 (FR) .................................. 01 04590

(51) Int. Cl.
*C02F 1/28* (2006.01)
*C02F 101/12* (2006.01)
*B01D 53/02* (2006.01)
*C07C 17/389* (2006.01)

(52) U.S. Cl. ...................... 210/660; 210/688; 210/912; 95/131; 95/133

(58) Field of Classification Search ................ 210/660, 210/688, 902, 912, 502.1; 95/131, 132, 133; 570/262; 502/414, 415
See application file for complete search history.

(56) References Cited

U.S. PATENT DOCUMENTS

| | | | | |
|---|---|---|---|---|
| 3,691,239 A | * | 9/1972 | Hackett et al. | .............. 570/262 |
| 4,053,558 A | * | 10/1977 | Campbell | ............... 423/240 R |
| 4,444,899 A | | 4/1984 | Yamada et al. | ............... 502/64 |
| 5,288,849 A | * | 2/1994 | Garcin et al. | ............... 528/482 |
| 5,316,998 A | | 5/1994 | Lee et al. | .................... 502/415 |

FOREIGN PATENT DOCUMENTS

| | | | |
|---|---|---|---|
| FR | 2 774 606 | | 8/1999 |
| GB | 1 223 238 | | 2/1971 |
| GB | 1380497 | * | 1/1975 |
| JP | 2000203829 | | 7/2000 |

OTHER PUBLICATIONS

International Search Report PCT/FR02/01070—Dated Jun. 14, 2002—H. Bertram Authorized Officer—3 Pages.

* cited by examiner

*Primary Examiner*—Matthew O. Savage
(74) *Attorney, Agent, or Firm*—Welsh & Katz, Ltd.

(57) ABSTRACT

The invention relates to a method for eliminating metal halides which are present in a liquid or gaseous, organic or non-organic effluent. According to the invention, the elimination is carried out by absorption of said metal halides on alumina agglomerates. The inventive method is characterised in that: the specific surface area of said agglomerates is between 50 and 350 m$^2$/g, preferably between 70 and 300 m$^2$/g and, better still, between 80 and 250 m$^2$/g; and the $V_{80A}$ thereof is greater than or equal to 20 ml/100 g, preferably greater than or equal to 25 ml/100 g, better still greater than or equal to 30 ml/100 g and, optimally, greater than or equal to 35 ml/100 g.

15 Claims, 1 Drawing Sheet

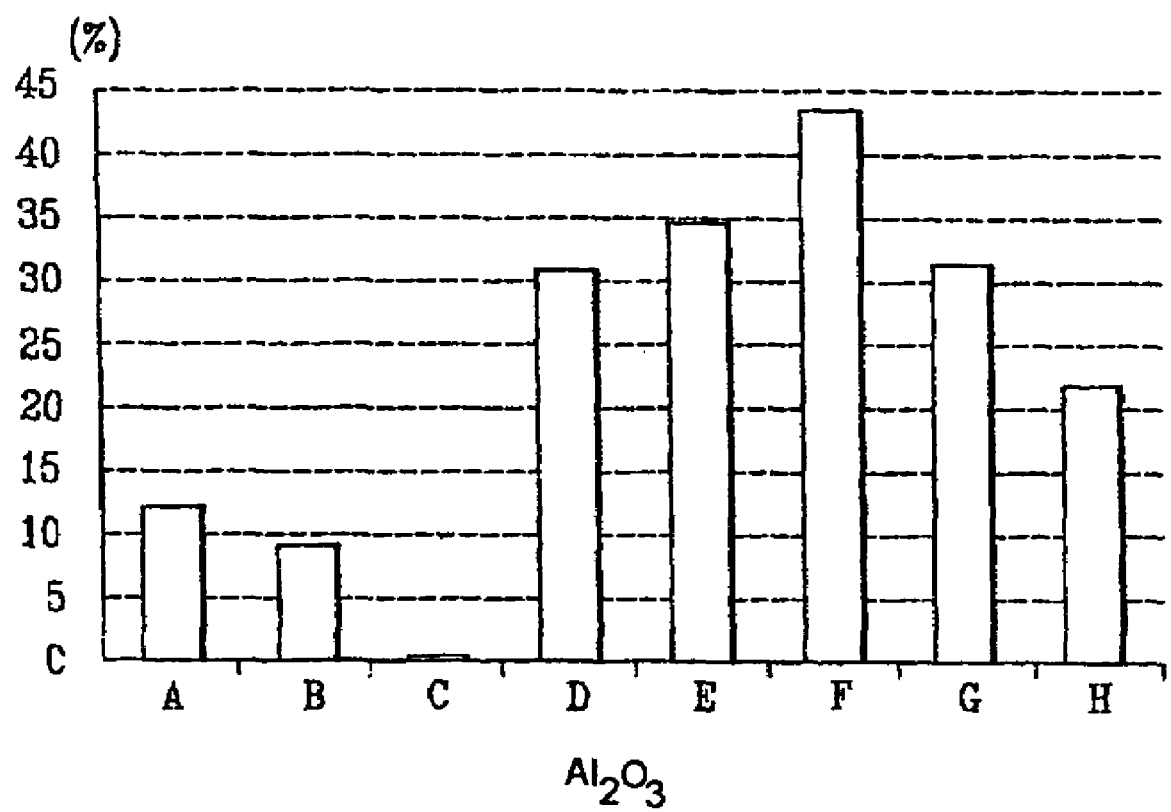

METHOD FOR ELIMINATING METAL HALIDES THAT ARE PRESENT IN A LIQUID OR GASEOUS, ORGANIC OR NON-ORGANIC EFFLUENT

The invention relates to the field of the elimination of impurities contained in organic or non-organic industrial effluents in the liquid or gaseous state. More precisely, it relates to the elimination of impurities consisting of metal halides contained in these effluents by absorption on alumina agglomerates.

Many gaseous or liquid industrial effluents contain impurities that it is desirable to eliminate. These impurities may pose problems of various types. Among these mention may be made of:

- interference with processes in which the effluent participates, for example formation of undesirable products or inhibition or poisoning of a catalyst;
- degradation of the quality of the final product resulting from a lack of purity, from undesirable coloration, etc.; and
- formation of industrial waste coming from treatment of the effluent, said waste being difficult to reprocess and therefore posing environmental problems.

It is known to improve the purity of certain liquid or gaseous, organic or non-organic industrial effluents by passing them over a mineral material, such as alumina, that retains certain impurities by adsorption on its surface. In particular, it is known to use alumina agglomerates to purify industrial effluents containing metal halides in trace quantities that it is desired to eliminate. It is usually accepted that these alumina particles must have a high specific surface area and therefore predominantly pores of very small size.

The object of the invention is to propose a method of purifying industrial effluents containing metal halides by selective adsorption on alumina, using forms of alumina that are relatively inexpensive to manufacture but nevertheless are extremely effective for the application envisioned, much more effective than the alumina particles for this purpose in the prior art.

For this purpose, the subject of the invention is a method of eliminating metal halides that are present in a liquid or gaseous, organic or non-organic effluent, in which this elimination is carried out by adsorption of said metal halides on alumina agglomerates, characterized in that:

said agglomerates have a specific surface area of between 50 and 350 $m^2/g$, preferably between 70 and 300 $m^2/g$ and even more preferably between 80 and 250 $m^2/g$; and in that said agglomerates have a $V_{80Å}$ of greater than or equal to 20 ml/100 g, preferably greater than or equal to 25 ml/100 g, even more preferably greater than or equal to 30 ml/100 g and optimally greater than or equal to 35 ml/100 g.

Preferably, said agglomerates have a $V_{400Å}$ of greater than or equal to 10 ml/100 g, preferably greater than or equal to 15 ml/100 g and even more preferably greater than or equal to 20 ml/100 g.

Preferably, said agglomerates have a $V_{37Å}$ of greater than or equal to 45 ml/100 g and preferably greater than or equal to 55 ml/100 g.

Said agglomerates may include one or more dopant compounds selected from compounds of alkali metals, alkaline-earth metals and rare earths, having a maximum content of 20%, preferably less than 10%.

Said agglomerates may be in the form of beads, preferably having a diameter of less than or equal to 8 mm and more preferably between 1 and 5 mm.

Said agglomerates may be in the form of extruded materials, for example with a cylindrical or polylobate shape.

Said extruded materials preferably have an inscribed diameter of their cross section of less than or equal to 4 mm.

Said alumina agglomerates may be in the form of powder.

In one particular application of the invention, said effluent is found downstream of a polyvinyl chloride production unit. The medium may then be based on dichloroethylene and said metal halide is ferric chloride.

As will have been understood, the invention consists in using, as selective adsorbent materials, a class of alumina agglomerates exhibiting particular characteristics in terms of both specific surface area and of porous structure. Surprisingly, in considering what had previously been determined experimentally, these agglomerates must have a relatively low specific surface area and a porosity profile in which pores of very small diameter do not necessarily represent a very large volume. However, these agglomerates possess remarkably high adsorbent properties with respect to metal halides contained in liquid or gaseous, organic or non-organic industrial effluents (it being possible, for example, for the latter to be aqueous solutions).

The invention will be more clearly understood from the description that follows, given with reference to the single appended figure. This shows, for various alumina agglomerates according to the invention and various control alumina agglomerates, the degree of elimination (in percent) of the ferric chloride contained in a ferric chloride solution in acetophenone brought into contact with an alumina agglomerate after 37 hours of reaction.

A preferential, but in no way limiting, application of the invention is downstream of a polyvinyl chloride (PVC) production line. After polymerization of the PVC, a residual dichloroethylene-based medium may remain which contains traces of ferric chloride. This ferric chloride must be eliminated before such a residual medium is recycled. It is also known to carry out this elimination by adsorption on alumina agglomerates such as those mentioned later with regard to the reference materials. It will be seen that the use, for this purpose, of one particular class of alumina agglomerates substantially improves the efficiency of a ferric chloride elimination operation.

The alumina agglomerates used within the context of the method of eliminating metal halides according to the invention must necessarily have a specific surface area of between 50 and 350 $m^2/g$, preferably between 70 and 300 $m^2/g$ and advantageously between 80 and 250 $m^2/g$. Also necessarily, they have a volume occupied by pores with a diameter of greater than or equal to 80 Å (denoted in short by the notation $V_{80Å}$) of greater than or equal to 20 ml/100 g, preferably greater than or equal to 25 ml/100 g, advantageously greater than or equal to 30 ml/100 g or even than greater than or equal to 35 ml/100 g.

It will be noted that the presence of pores having a diameter of less than 80 Å is of only little importance within the context of the invention. The little importance ascribed to such microporosity goes, as mentioned, counter to what has been commonly accepted hitherto.

According to a preferred variant of the invention, the volume occupied by the pores having a diameter of greater than or equal to 400 Å ($V_{400Å}$) is greater than or equal to 10 ml/100 g, advantageously greater than or equal to 20 ml/100 g.

The $V_{80Å}$ and $V_{400Å}$ may be determined by a conventional mercury porosimetry method.

For this purpose, the alumina specimen is first placed in a column into which mercury under a pressure P is introduced. Since mercury does not wet alumina, its penetration or non-penetration into the pores of the specimen having a given diameter depends on the value of P. In order to be filled, the finest pores require a higher pressure P to be established than for filling the coarser pores. By measuring the amount of mercury penetrating the specimen for various values of P, it is possible to determine the volume occupied by the pores of diameter greater than given values of this diameter.

According to one particular form of the invention, the alumina agglomerates may be chemically modified by the addition of alkali metal or alkaline-earth metal compounds, or rare-earth compounds, or a mixture of such compounds.

Preferably, compounds based on sodium, potassium, calcium, magnesium or lanthanum are chosen. Sodium is a preferred example, and may be introduced in the form of one or more precursors of its oxide $Na_2O$.

The addition of one or more dopant compounds may be carried out before or after the forming operation or during it.

The dopant compounds are present in the alumina agglomerate with a total mass content of less than 20%, preferably less than 10%.

These dopant compounds enhance the adsorbent properties of the surface of the alumina agglomerates with respect to the metal halide molecules that it is desired to eliminate.

The alumina may be used in powder form, but preferably it is used after a forming step. Beads, advantageously with a diameter of less than 8 mm, preferably mostly between 1 and 5 mm, constitute a preferred form of the alumina agglomerates according to the invention. Another preferred form is that of cylindrical or polylobate extrudates, the inscribed diameter of their cross section preferably being less than 4 mm.

The beads may be obtained by means of a rotational technique, by agglomeration of an alumina powder in a pelletizer or drum. This type of process makes it possible to obtain, in a known manner, beads with controlled pore distributions and diameters, these distributions and dimensions being, in general, created during the agglomeration step. The porosity may be created by various means, such as the choice of the particle size of the alumina powder or the agglomeration of several alumina powders of different particle sizes. Another method consists in mixing with the alumina powder, before or during the agglomeration step, a compound, called a pore former, that disappears when it is heated and thus creates porosity in the beads. As pore-former compounds used, mention may be made, by way of example, of wood flour, charcoal, sulfur, tars, plastics or emulsions of plastics, such as polyvinyl chloride and polyvinyl alcohols, naphthalene or the like. The amount of pore-former compounds added is determined by the desired volume. One or more heat treatments then complete the operation of forming the beads.

The extrudates may be obtained by mixing and then extruding an alumina gel or an alumina powder or a mixture of various raw materials.

The initial alumina powder may be obtained conventionally by rapid dehydration of an aluminium hydroxide (for example, hydrargilite).

The addition of one or more dopant compounds may be carried out before or after the forming operation or during the latter.

As examples, the ferric chloride ($FeCl_3$) adsorption results for various control alumina agglomerates and for alumina agglomerates having the characteristics required by the method according to the invention will be compared.

Eight alumina agglomerates were considered, the use of aluminas A, B and C forming a part of the prior art and the use of aluminas D, E, F, G and H corresponding to the invention.

100 ppm of $FeCl_3 \cdot 6H_2O$ were placed in a beaker containing 250 ml of acetophenone. Next, 1 g of alumina pretreated at 300° C., in the form of beads or extruded materials, was then added. The beaker was then isolated from the ambient air, shielded from light in order to avoid any degradation of the solvent (which was photosensitive) and subjected to magnetic stirring, the beads or extrudates being isolated from the bar magnet so as to avoid any undesirable attrition during the experiment.

The description of the alumina agglomerates used is given in table I, in which the diameters are in mm, the specific surface areas are in $m^2/g$ and the porosities are in ml/100 g. Table I mentions, apart from the abovementioned parameters, the $V_{37Å}$ of each agglomerate, that is to say the volume occupied by the pores having a diameter greater than or equal to 37 Å. The difference between $V_{37Å}$ and $V_{80Å}$ is representative of the amount of pores with very small diameters of the agglomerate tested. Finally, the $Na_2O$ content of the agglomerates, expressed in ppm, is mentioned.

TABLE I

Characteristics of the alumina agglomerates tested

| | Controls | | | Invention | | | | |
|---|---|---|---|---|---|---|---|---|
| Alumina | A | B | C | D | E | F | G | H |
| Form | Beads | Beads | Beads | Extrudates | Beads | Beads | Extrudates | Beads |
| Diameter | 1.4-2.8 | 1.4-2.8 | 2-4 | 1.2 | 2.0-2.8 | 1.4-2.8 | 1.2 | 2.0-2.8 |
| Specific surface area | 337 | 257 | 6 | 266 | 196 | 150 | 251 | 172 |
| $V_{37Å}$ | 35.6 | 37.2 | 53.5 | 68.4 | 68.0 | 102.3 | 59.8 | 58.4 |
| $V_{80Å}$ | 14.1 | 9.4 | 53.4 | 48.9 | 57.5 | 98.5 | 41.5 | 46.5 |
| $V_{400Å}$ | 5.3 | 4.6 | 53.2 | 5.8 | 20.0 | 53.7 | 5.4 | 15.2 |
| $Na_2O$ | 3500 | 20000 | 700 | 500 | 700 | 700 | 20000 | 20000 |

The iron chloride concentration of the acetophenone solution was monitored by UV-visible analysis, in particular by monitoring the change in absorbance at the wavelength of 378 nm.

After 37 hours of reaction at room temperature, the degrees of elimination of iron chloride from the organic solution were thus determined, and these are plotted in the diagram shown in FIG. 1.

The aluminas used in the prior art show an adsorption potential markedly inferior to that of the aluminas used in the method according to the invention.

The ferric chloride adsorption efficiency of control alumina C, having only large-diameter pores and a very low specific surface area, is very mediocre.

It should be noted that the aluminas of the method according to the invention have a specific surface area that is not particularly high: it is of the same order of magnitude or substantially less than that of control alumina B and substantially less than that of control alumina A.

Compared with control aluminas A and B, that have a similar or higher specific surface area, the aluminas according to the invention are distinguished by their relatively high $V_{80Å}$. However, it should also be noted that, in many cases, the aluminas according to the invention exhibit a small difference between $V_{80Å}$ and $V_{37Å}$, this being an indicator of the fact that they have few pores of very small size. In particular, this is the case for alumina F that gives the best ferric chloride adsorption results. However, it will be preferable for $V_{37Å}$ to be usefully at least 45 ml/100 g, preferably greater than 55 ml/100 g. It should also be noted that this alumina F has a high $V_{400Å}$, and therefore large-diameter pores present at a relatively high quantity. This all results in quite a low specific surface area, which nevertheless does not compromise the quality of the results obtained, quite to the contrary. These results therefore go counter to what was commonly accepted as having to constitute preferred characteristics of the alumina agglomerates in their envisaged application of adsorbing metal chlorides.

Finally, it should be noted that the aluminas of the examples according to the invention do not have very high $Na_2O$ (dopant compound) contents; they are at most 2%. Despite this, they exhibit ferric chloride adsorption properties substantially higher than the control aluminas of comparable $Na_2O$ content. This clearly shows that, for this application, the role of the porosity of the agglomerates is predominant, the doping of these agglomerates by alkali or alkaline-earth metal compounds being merely a variant of the invention.

The invention is not limited to the specific examples that have been mentioned, namely the adsorption of ferric chloride from an effluent based on dichloroethylene or acetophenone. The use of alumina agglomerates as described for the adsorption of metal halides may be envisioned for the treatment of any gaseous or liquid, organic or non-organic effluents. It is particularly applicable to aqueous solutions.

The invention claimed is:

1. A method of eliminating metal halides that are present in a liquid or gaseous, organic or non-organic effluent, in which this elimination is carried out by adsorption of said metal halides on alumina agglomerates, wherein:
   said agglomerates have a specific surface area of between 50 and 350 $m_2/g$;
   said agglomerates have a $V_{80Å}$ of at least 20 ml/100 g, a $V_{400Å}$ of at least 10 ml/100 g, and a $V_{37Å}$ of at least 45 ml/100 g; and
   said agglomerates include a dopant comprising $Na_2O$.

2. The method as claimed in claim 1 wherein said agglomerates are in the form of beads.

3. The method as claimed in claim 2, wherein said beads have a diameter of less than or equal to 8 mm.

4. The method as claimed in claim 1 wherein said agglomerates are in the form of extruded materials.

5. The method as claimed in claim 4, wherein said extruded materials are of cylindrical shape.

6. The method as claimed in claim 4, wherein said extruded materials are of polylobate shape.

7. The method as claimed in claim 4 wherein said extruded materials have an inscribed diameter of their cross section of less than or equal to 4 mm.

8. The method as claimed in claim 2, wherein said beads have a diameter of between 1 and 5 mm.

9. The method as claimed in claim 1 wherein said alumina agglomerates are in the form of powder.

10. The method as claimed in claim 1 wherein-said effluent is a dichloroethylene-based medium and in that said metal halide is ferric chloride.

11. A method as claimed in claim 1 of eliminating metal halides that are present in a liquid or gaseous, organic or non-organic effluent, in which this elimination is carried out by adsorption of said metal halides on alumina agglomerates, characterized in that wherein:
    said agglomerates have a specific surface area of between 50 and 350 $m^2/g$; and in that
    said agglomerates have a $V_{80Å}$ of greater than or equal to 30 ml/100 g.

12. The method as claimed in claim 1, wherein said agglomerates have a $V_{400Å}$ of at least 20 ml/100 g.

13. The method as claimed in claim 1 wherein said agglomerates have a $V_{37Å}$ of at least 55 ml/100 g.

14. The method of claim 1 wherein said dopant is present in the alumina agglomerate with a total mass content of less than 20%.

15. A method of eliminating metal halides that are present in a liquid or gaseous, organic or non-organic effluent, in which this elimination is carried out by adsorption of said metal halides on alumina agglomerates, wherein:
    said agglomerates have a specific surface area of between 50 and 350 $m^2/g$;
    said agglomerates have a $V_{80Å}$ of at least 20 ml/100 g;
    a $V_{400Å}$ of at least 10 ml/100 g and a $V_{37Å}$ of at least 45 ml/100 g; and
    said agglomerates have less than 2% dopant measured as $NaO_2$.

* * * * *